United States Patent
Tatsunari

(10) Patent No.: US 6,994,750 B2
(45) Date of Patent: Feb. 7, 2006

(54) FILM EVALUATING METHOD, TEMPERATURE MEASURING METHOD, AND SEMICONDUCTOR DEVICE MANUFACTURING METHOD

(75) Inventor: Toshitaka Tatsunari, Uji (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 278 days.

(21) Appl. No.: 10/415,435

(22) PCT Filed: Sep. 10, 2002

(86) PCT No.: PCT/JP02/09241

§ 371 (c)(1),
(2), (4) Date: Apr. 29, 2003

(87) PCT Pub. No.: WO03/023844

PCT Pub. Date: Mar. 20, 2003

(65) Prior Publication Data

US 2004/0023403 A1 Feb. 5, 2004

(30) Foreign Application Priority Data

Sep. 10, 2001 (JP) .............................. 2001-273132

(51) Int. Cl.
*C30B 25/14* (2006.01)

(52) U.S. Cl. .............................. 117/84; 117/85; 117/86; 117/101; 117/105

(58) Field of Classification Search .................. 117/84, 117/85, 86, 101, 105
See application file for complete search history.

(56) References Cited

U.S. PATENT DOCUMENTS

| | | | |
|---|---|---|---|
| 4,141,780 A * | 2/1979 | Kleinknecht et al. ......... | 117/85 |
| 4,581,576 A * | 4/1986 | Wang ......................... | 324/702 |
| 5,213,985 A * | 5/1993 | Sandroff et al. ............... | 438/7 |
| 5,461,559 A * | 10/1995 | Heyob et al. ................ | 700/29 |
| 5,463,977 A * | 11/1995 | Manada et al. ............... | 117/85 |
| 5,595,916 A | 1/1997 | Fujimura et al. | |
| 5,782,974 A * | 7/1998 | Sorensen et al. ............. | 117/82 |
| 6,074,485 A * | 6/2000 | Tsukamoto et al. ......... | 118/713 |
| 6,306,668 B1 * | 10/2001 | McKee et al. ................ | 438/7 |
| 6,679,946 B1 * | 1/2004 | Jackson et al. ............... | 117/84 |

FOREIGN PATENT DOCUMENTS

| | | |
|---|---|---|
| JP | 56-18440 | 2/1981 |
| JP | 57-186322 | 11/1982 |
| JP | 05-117867 | 5/1993 |
| JP | 5-249031 | 9/1993 |
| JP | 6-77301 | 3/1994 |

(Continued)

OTHER PUBLICATIONS

B. Flamme, "Investigation of Amorphous Low-Pressure Chemical-Vapor-Deposited Silicon Films by Ellipsometry", Siemens Forsch.-u. Entwickl.-Ber. Bd. 10, (1981), Nr. 1, pp. 48-52.

(Continued)

*Primary Examiner*—Robert Kunemund
(74) *Attorney, Agent, or Firm*—McDermott Will & Emery LLP

(57) ABSTRACT

Reference infrared-absorption spectrum patterns are prepared in advance as a database. The infrared-absorption spectrum pattern of a film targeted for measurement is measured using FT-IR spectroscopy. Subsequently, multivariate analysis is performed using PLS regression, based on the reference infrared-absorption spectrum patterns and the infrared-absorption spectrum pattern of the target film. The film-growing temperature and other factors are then computed in accordance with the analysis results.

19 Claims, 12 Drawing Sheets

FOREIGN PATENT DOCUMENTS

| | | |
|---|---|---|
| JP | 06/341952 | 12/1994 |
| JP | 07-188930 | 7/1995 |
| JP | 10-031039 | 2/1998 |
| JP | 10-056010 | 2/1998 |
| JP | 2000-088748 A | 3/2000 |
| WO | WO 99/57146 | 11/1999 |

OTHER PUBLICATIONS

M. Fried et al., "Optical Properties of Thermally Stabilized Ion Implantation Amorphized Silicon", Nuclear Instruments and Methods in Physics Research, B19/20, (1987), pp. 577-581.

* cited by examiner

FIG. 2

|  | WaveNumber [cm-1] | Absorbance [a.u.] |
|---|---|---|
| 380°C | 1087.8 | 0.6718 |
| 430°C | 1088.8 | 0.7038 |
| 480°C | 1089.2 | 0.7257 |

FIG. 12(a)

| Item | Settings |
|---|---|
| Infrared-absorption spectrum number | 50 |
| Maximum wavenumber [cm-1] | 1600 |
| Minimum wavenumber [cm-1] | 700 |
| Number of divisions for infrared absorption spectrum | 467 |

FIG. 12(b)

| Item | Calculation result |
|---|---|
| Correct coefficient | 0.98 |

FIG. 13

| Infrared absorption spectrum number | Temperature in database [°C] | Analysis temperature [°C] | Difference [°C] | Error rate [%] | Spectral residual | Reliability of analysis value |
|---|---|---|---|---|---|---|
| 1 | 384.2 | 383.0 | 1.2 | 0.3 | 0.011037 | 0.02642 |
| 2 | 384.8 | 387.3 | -2.5 | -0.7 | 0.007640 | 0.11400 |
| 3 | 389.7 | 389.6 | 0.1 | 0.0 | 0.008367 | 0.00037 |
| 4 | 391.3 | 395.0 | -3.7 | -0.9 | 0.009091 | 0.42758 |
| 5 | 390.6 | 389.8 | 0.8 | 0.2 | 0.011399 | 2.02860 |
| 6 | 400.8 | 401.3 | -0.5 | -0.2 | 0.005355 | 0.43884 |
| 7 | 449.0 | 446.7 | 2.2 | 0.5 | 0.003811 | 0.22165 |
| 8 | 451.2 | 454.1 | -2.9 | -0.6 | 0.005593 | 0.47891 |
| 9 | 451.7 | 455.1 | -3.4 | -0.7 | 0.010259 | 1.63500 |
| 10 | 452.5 | 452.9 | -0.5 | -0.1 | 0.005513 | 0.46526 |
| 11 | 452.6 | 447.9 | 4.7 | 1.0 | 0.003139 | 0.15025 |
| 12 | 452.6 | 454.7 | -2.1 | -0.5 | 0.005443 | 0.45350 |
| 13 | 452.9 | 449.6 | 3.3 | 0.7 | 0.005057 | 0.39113 |
| 14 | 453.1 | 449.8 | 3.3 | 0.7 | 0.009709 | 1.46130 |
| 15 | 453.4 | 455.2 | -1.8 | -0.4 | 0.006671 | 0.68316 |
| 16 | 453.6 | 450.7 | 2.9 | 0.6 | 0.007620 | 0.89375 |
| 17 | 453.7 | 457.1 | -3.4 | -0.7 | 0.006291 | 0.60702 |
| 18 | 453.8 | 456.5 | -2.6 | -0.6 | 0.005057 | 0.39111 |
| 19 | 468.4 | 470.3 | -1.9 | -0.4 | 0.005505 | 0.46393 |
| 20 | 471.2 | 469.0 | 2.1 | 0.5 | 0.003871 | 0.22876 |
| 21 | 472.3 | 473.8 | -1.5 | -0.3 | 0.009205 | 1.31100 |
| 22 | 474.1 | 477.6 | -3.5 | -0.7 | 0.006494 | 0.64708 |
| 23 | 474.7 | 478.7 | -4.0 | -0.8 | 0.010829 | 1.82610 |
| 24 | 476.6 | 474.8 | 1.8 | 0.4 | 0.004126 | 0.26001 |
| 25 | 476.6 | 473.8 | 2.8 | 0.6 | 0.004749 | 0.34471 |
| 26 | 476.8 | 474.0 | 2.7 | 0.6 | 0.007962 | 0.97685 |
| 27 | 477.0 | 477.8 | -0.8 | -0.2 | 0.010042 | 1.56540 |
| 28 | 477.1 | 477.3 | -0.2 | 0.0 | 0.005840 | 0.52250 |
| 29 | 477.6 | 474.9 | 2.7 | 0.6 | 0.005356 | 0.43905 |
| 30 | 477.7 | 477.6 | 0.0 | 0.0 | 0.011444 | 2.04510 |
| 31 | 478.9 | 483.1 | -4.2 | -0.9 | 0.005277 | 0.42605 |
| 32 | 481.5 | 484.5 | -3.0 | -0.6 | 0.007830 | 0.94431 |
| 33 | 481.6 | 477.3 | 4.3 | 0.9 | 0.007784 | 0.93315 |
| 34 | 487.9 | 488.6 | -0.6 | -0.1 | 0.006325 | 0.61360 |
| 35 | 488.1 | 483.4 | 4.7 | 1.0 | 0.005065 | 0.39245 |
| 36 | 488.6 | 490.8 | -2.2 | -0.4 | 0.004240 | 0.27461 |
| 37 | 488.9 | 491.0 | -2.1 | -0.4 | 0.004092 | 0.25567 |
| 38 | 491.1 | 493.8 | -2.7 | -0.6 | 0.007371 | 0.83566 |
| 39 | 491.2 | 494.8 | -3.6 | -0.7 | 0.005702 | 0.49799 |
| 40 | 491.3 | 493.6 | -2.4 | -0.5 | 0.004176 | 0.26634 |
| 41 | 491.6 | 493.7 | -2.1 | -0.4 | 0.012865 | 2.60240 |
| 42 | 491.6 | 494.2 | -2.6 | -0.5 | 0.009386 | 1.36400 |
| 43 | 491.6 | 494.1 | -2.5 | -0.5 | 0.019477 | 6.22920 |
| 44 | 491.6 | 491.8 | -0.2 | 0.0 | 0.013010 | 2.66300 |
| 45 | 502.1 | 503.2 | -1.0 | -0.2 | 0.004600 | 0.32331 |
| 46 | 503.3 | 504.2 | -0.9 | -0.2 | 0.010761 | 1.80290 |
| 47 | 503.8 | 501.6 | 2.2 | 0.4 | 0.011306 | 1.99490 |
| 48 | 503.9 | 501.2 | 2.7 | 0.5 | 0.008634 | 1.15110 |
| 49 | 504.3 | 507.8 | -3.5 | -0.7 | 0.013618 | 2.92730 |
| 50 | 504.5 | 509.2 | -4.7 | -0.9 | 0.017270 | 4.81660 |

FILM EVALUATING METHOD, TEMPERATURE MEASURING METHOD, AND SEMICONDUCTOR DEVICE MANUFACTURING METHOD

TECHNICAL FIELD

The present invention relates to a film evaluation method, a temperature measurement method and a semiconductor device fabrication method, applicable to fabrication of various kinds of transistors and semiconductor memories and other semiconductor devices that are incorporated into electronic equipment.

BACKGROUND ART

In recent years, as the degree of integration of, and the performance of, semiconductor devices have been increasing, fluorine-doped silicon oxide films (hereinafter referred to as "FSG films") having low relative dielectric constants are being used for interlevel dielectric films in which multilevel interconnects are formed. Generally, an FSG film is grown in an HDP-CVD (high density plasma-chemical vapor deposition) apparatus that is suitable for filling of the fine interconnection vias.

The HDP-CVD apparatus, however, has a structure in which an electrostatic chuck is employed to hold the wafer, and is thus encumbered by a problem in that the film-growing temperature cannot be monitored. In addition, the film-growing temperature in the HDP-CVD apparatus, which is determined by factors such as RF power that is applied during film growth, cannot be measured accurately because it is difficult to measure the actual temperature using a silicon substrate that comes with a thermocouple, for example.

The present inventors therefore used the temperature measurement technique described in International Publication No. WO99/57146 to measure film-growing temperature in an HDP-CVD apparatus. In this technique, temperature measurement is carried out based on the rate at which a silicon amorphous layer on a silicon substrate is recovered.

Now, in addition to the foregoing international publication, which relates to spectroscopic ellipsometry, the following documents are relevant.

(1) Nuclear Instruments and Methods in Physics Research, B19/20, (1987), pp. 577–581.

(2) Japanese Laid-Open Pat. Publication No. H06-077301.

(3) Siemens Forsch. -u.Entwickl. -Ber.Bd. 10, (1981), Nr. 1, pp. 48–52.

(4) Japanese Laid-Open Pat. Publication No. H05-249031.

PROBLEMS THAT THE INVENTION INTENDS TO SOLVE

Nevertheless, the conventional temperature measurement technique based on the rate at which a silicon amorphous layer is recovered, requires advance preparations such as performing a procedure in which the amorphous silicon layer is formed on the silicon substrate beforehand. Further, in order to measure film-growing temperature in an HDP-CVD apparatus, operation of the HDP-CVD apparatus has to be stopped mid-process to form a film under conditions exclusively for temperature measurement. In other words, the CVD apparatus has to be placed off-line.

DISCLOSURE OF INVENTION

An object of the present invention is to easily measure the characteristics or film-growing temperature of a film that has been formed using a film-growing apparatus, without placing the apparatus off-line, that is, without causing deterioration in the productivity of the apparatus.

An inventive film evaluation method includes the steps of: (a) irradiating with electromagnetic waves a substrate on which a film is formed, thereby measuring an absorption spectrum for the electromagnetic waves, and (b) calculating from the shape of the absorption spectrum a specific value corresponding to the quality of the film.

According to the inventive method, since the characteristics of a film can be detected using an electromagnetic-waves absorption spectrum, materials that can be used for film-growing apparatus control and determination of the quality of films, e.g., in semiconductor devices, can be obtained.

In the step (a), the electromagnetic waves may be infrared radiation, and in the step (b), the specific value may be calculated from the shape of an absorption spectrum for the infrared radiation.

In that case, a plurality of reference infrared-absorption spectra may be prepared in advance in accordance with film quality level, and in the step (b), the reference infrared-absorption spectra and the infrared absorption spectrum of the film may be compared with each other, thereby calculating the specific value. Then, the specific value can be obtained in an easy manner.

In the step (b), multivariate analysis may be performed based on the shapes of the reference infrared-absorption spectra and of the infrared absorption spectrum, thereby calculating the specific value. Then, the specific value can be calculated with high accuracy using PLS (partial least squares) regression or other techniques.

In the step (a), preferably, an infrared absorption spectrum of the substrate, which has been measured in advance, is subtracted from the infrared absorption spectrum of the film and the substrate, thereby obtaining an infrared absorption spectrum of the film alone.

An inventive temperature measuring method includes the steps of: (a) irradiating with electromagnetic waves a substrate on which a film is formed, thereby measuring an absorption spectrum for the electromagnetic waves, and (b) calculating from the shape of the absorption spectrum a temperature at which the film has been grown.

According to the inventive method, since the film-growing temperature of a film can be detected using an electromagnetic-waves absorption spectrum, materials that can be used for film-growing apparatus control and determination of the quality of films, e.g., in semiconductor devices, can be obtained.

In the step (a), the electromagnetic waves may be infrared radiation, and in the step (b), the temperature at which the film has been grown may be calculated from the shape of an absorption spectrum for the infrared radiation.

A plurality of reference infrared-absorption spectra may be prepared in advance in accordance with film-growing temperature, and in the step (b), the reference infrared-absorption spectra and the infrared absorption spectrum of the film may be compared with each other, thereby calculating the temperature at which the film has been grown. Then, the temperature at which the film has been grown can be calculated easily.

In the step (b), multivariate analysis may be performed based on the shapes of the reference infrared-absorption spectra and of the infrared absorption spectrum, thereby calculating the temperature at which the film has been grown. Then, the temperature at which the film has been grown can be calculated accurately using PLS regression and other techniques.

In the step (a), preferably, an infrared absorption spectrum of the substrate, which has been measured in advance, is subtracted from the infrared absorption spectrum of the film and the substrate, thereby obtaining an infrared absorption spectrum of the film alone.

In the step (a), the substrate may be placed in a film-growing apparatus in advance, and the film is formed on the substrate, and in the step (b), the temperature at which the film has been grown may be calculated as a temperature inside the film-growing apparatus. Then, the temperature in the film-growing apparatus (chamber) can be quickly measured using an in-line wafer or a control wafer, without attaching a sensor to the wafer or taking another measure.

A first inventive method for fabricating a semiconductor device including a film as an element forming the device, includes the steps of: (a) forming the film on an underlying wafer placed in a film-growing apparatus, (b) irradiating with infrared radiation the wafer on which the film has been formed, thereby measuring an infrared absorption spectrum, (c) calculating from the shape of the infrared absorption spectrum a specific value corresponding to the quality of the film, and (d) controlling conditions determined for the film-growing apparatus, in accordance with the specific value calculated in the step (c).

According to the inventive method, in-line non-destructive detection of the characteristics of a film can be carried out using an electromagnetic-waves absorption spectrum, and results of the detection can be used for film-growing apparatus control. Thus, specific values can be measured in all film growing processes without causing any deterioration in productivity, thereby enabling conditions determined for a film-growing apparatus to be controlled.

A plurality of reference infrared-absorption spectra may be prepared in advance in accordance with film quality level, and in the step (c), the reference infrared-absorption spectra and the infrared absorption spectrum of the film measured in the step (b) may be compared with each other, thereby calculating the specific value. Then, the process steps can be controlled in an easy manner.

In the step (c), multivariate analysis may be performed based on the shapes of the reference infrared-absorption spectra and of the infrared absorption spectrum, thereby calculating the specific value. Then, process control can be performed accurately.

A second inventive method for fabricating a semiconductor device including a film as an element forming the device, includes the steps of: (a) forming the film on an underlying wafer placed in a film-growing apparatus, (b) irradiating with infrared radiation the wafer on which the film has been formed, thereby measuring an infrared absorption spectrum, (c) calculating from the shape of the infrared absorption spectrum a temperature at which the film has been grown, and (d) controlling conditions determined for the film-growing apparatus, in accordance with the temperature at which the film has been grown, the temperature calculated in the step (c).

According to the inventive method, in-line non-destructive detection of the temperature at which a film has been grown can be carried out using an electromagnetic-waves absorption spectrum, and results of the detection can be used for film-growing apparatus control. Therefore, film-growing temperatures can be measured in all film growing processes without causing any deterioration in productivity, thereby enabling conditions determined for a film-growing apparatus to be controlled.

A plurality of reference infrared-absorption spectra may be prepared in advance in accordance with film-growing temperature, and in the step (c), the reference infrared-absorption spectra and the infrared absorption spectrum of the film measured in the step (b) may be compared with each other, thereby calculating the temperature at which the film has been grown. Then, process steps can be controlled easily.

In the step (c), multivariate analysis may be performed based on the shapes of the reference infrared-absorption spectra and of the infrared absorption spectrum, thereby calculating the temperature at which the film has been grown. Then, process control can be carried out accurately.

BRIEF DESCRIPTION OF DRAWINGS

FIG. 2 is a table showing wavelengths indicating the maximum absorption values, as well as the maximum absorption values at the respective peaks of the infrared absorption spectra shown in FIGS. 1(a) and 1(b).

FIGS. 12(a) and 12(b) are respectively tables showing exemplary settings in a constructed database and a calculation result.

FIG. 13 is a table showing results of examination of temperatures in the constructed database and analysis temperatures.

BEST MODE FOR CARRYING OUT THE INVENTION

Used in the following embodiments are techniques of measuring, by FT-IR (Fourier-transform infrared) spectroscopy, the infrared absorption spectrum of a substrate on which a film is formed, and of performing multivariate analysis of the infrared absorption spectrum based on pattern recognition, using PLS (partial least squares) regression.

First Embodiment

Figure 1A:
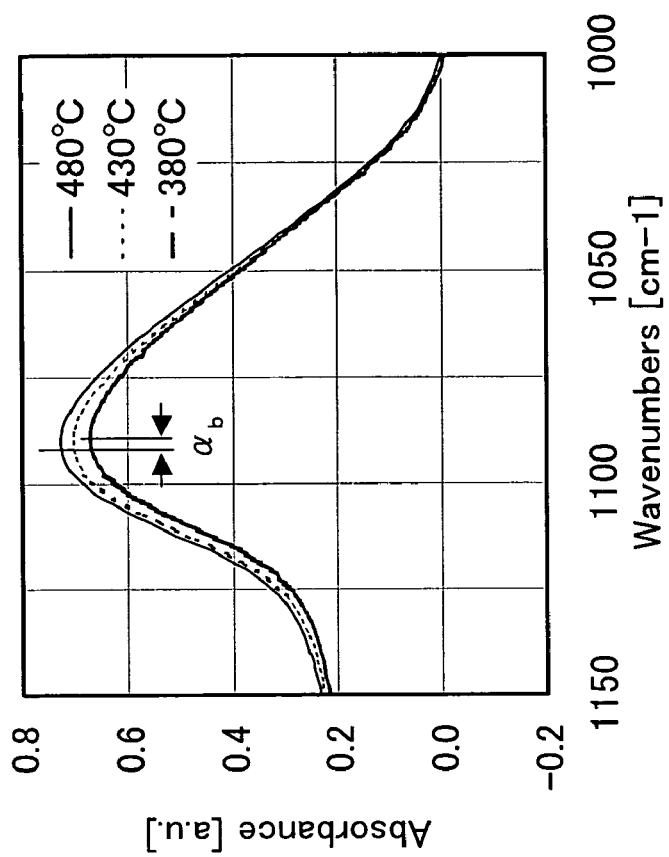
FIGS. 1(a) and 1(b) are respectively a view showing the infrared absorption spectra of FSG films and an enlarged view showing parts of the spectra in the vicinity of their peaks, measured by FT-IR spectroscopy.
Figure 1B:
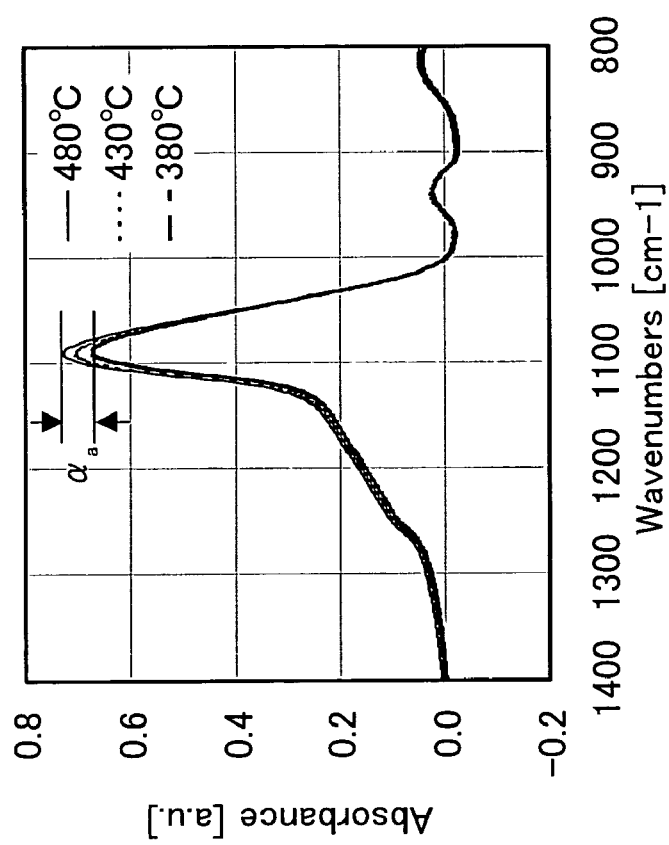

FIGS. 1(a) and 1(b) are respectively a view showing the infrared absorption spectra of FSG (fluorine-containing silicon oxide) films and an enlarged view showing parts of the spectra in the vicinity of their peaks, measured by FT-IR spectroscopy using the film-growing temperature in an HDP-CVD apparatus as a parameter.

The infrared absorption spectra of the FSG films shown in FIGS. 1(a) and 1(b), which are the infrared absorption spectra of FSG films grown on respective silicon substrates, are measured by the following procedure.

Silicon substrates are in general permeable to infrared radiation. When one face of a silicon substrate is irradiated with infrared radiation, a certain proportion of the infrared radiation is absorbed by the silicon substrate, following which the infrared radiation that has permeated the silicon substrate is transmitted through the other face of the silicon substrate. Taking advantage of this property, the reverse or obverse face of a wafer is irradiated with infrared coherent light with a diameter of some 5 mm, for example, in the perpendicular direction. Using FT-IR spectroscopy, coherent light between the intensity of the incident infrared radiation and the intensity of the infrared radiation that has transmitted through the wafer is detected; and a function for the intensity of the coherent light in relation to the optical path difference is Fourier-transformed to calculate a function in relation to the wavenumbers, which becomes the first infrared absorption spectrum.

Next, the silicon substrate is placed inside an HDP-CVD apparatus and an FSG film is grown on the silicon substrate to a given thickness. The same spot on the wafer is then irradiated with infrared radiation under substantially the same conditions as described above. Using FT-IR spectroscopy, the ratio of the intensity of the infrared radiation incident on the FSG film and the silicon substrate, to the intensity of the infrared radiation that has permeated both the film and substrate is measured wavelength by wavelength. This becomes the second infrared absorption spectrum. The first infrared absorption spectrum is subtracted from the second infrared absorption spectrum to calculate the infrared absorption of the FSG film alone. In this manner, the infrared absorption spectrum of the silicon substrate is subtracted from the combined infrared absorption spectrum of the FSG film and silicon substrate, thereby enabling the infrared absorption spectrum of the FSG film alone as desired to be obtained.

In the following description, the infrared absorption spectra of FSG films are measured by the same procedure, except where specifically noted. Nevertheless, it should be understood that thin films that are subjects for measuring infrared absorption spectrum in the present invention are not limited to FSG films, nor are the methods for fabricating semiconductor devices limited to methods using an HDP-CVD apparatus. Likewise, the substrate underlying the thin film is not limited to a silicon substrate. Furthermore, the infrared-absorption spectrum measurement method is not limited to FT-IR spectroscopy.

Moreover, if the silicon substrate thickness, phosphorous concentration and oxygen concentration are identical, the same result as that acquired when the first infrared absorption spectrum is subtracted from the second infrared absorption spectrum, can be obtained by measuring the second infrared absorption spectrum alone.

It should be also understood that in the present invention the infrared absorption spectra are measured by an infrared spectroscopy analytical instrument for semiconductor (IR-EPOCH 2000), as an FT-IR based instrument, manufactured by Newly Instruments, Inc.

As can be seen from FIGS. 1(a) and 1(b), if the FSG film-growing temperatures differ, the resultant infrared absorption spectra differ in shape; in particular, the maximum absorption values and the wavelengths that indicate the maximum absorption values differ in the peak regions. The present inventors made various studies as to whether there might be a method, other than the above-mentioned known temperature-measurement method based on the rate at which an amorphous silicon film is recovered, for monitoring film-growing temperature in an HDP-CVD apparatus. The cumulative result of their studies was the discovering that infrared absorption spectra (which in this embodiment are the infrared absorption spectra measured by FT-IR spectroscopy) differ depending on the thin-film growing temperature (which in this embodiment is the film-growing temperature in an HDP-CVD apparatus).

It will be described why infrared absorption spectra measured by FT-IR spectroscopy differ depending on the film growing temperature in an HDP-CVD apparatus.

An FSG film formed in an HDP-CVD apparatus presumably becomes a more perfect silicon oxide film as the film-growing temperature is raised. Specifically, analysis, by FT-IR spectroscopy, of FSG films that have been grown to the same thickness at different temperatures has resulted in the findings of: (1) the existence of a variation ($\alpha_a$) between the heights of the peaks, which is caused by difference in degree as to how perfect the resultant FSG films are, each peak showing the total amount of absorption by, e.g., Si—O bonds (see FIG. 1(a)); and (2) the existence of a difference ($\alpha_b$) between the locations of the peaks for, e.g., the Si—O bonds, which difference is created by quality variations between the FSG films due to the different film-growing temperatures (see FIG. 1(b)).

FIG. 2 is a table showing wavelengths indicating the maximum absorption values, as well as the maximum absorption values at the respective peaks of the infrared absorption spectra shown in FIGS. 1(a) and 1(b). In the range shown in FIG. 2, as the film-growing temperatures are raised, both the maximum absorption values and the wavenumbers indicating the maximum absorption values increase.

More specifically, the present inventors noted that the FSG films that have been grown at different temperatures differ from each other in the height and location of their peaks for, e.g., the Si—O bonds, that is, in the shape of the absorption peaks, resulting in the discovery of the fact that film-growing temperatures in an HDP-CVD apparatus can be detected using a new, unconventional method using FT-IR spectroscopy. The reason why the different film-growing temperatures result in the different absorption spectrum shapes is presumably that bonds such as Si—O, Si=O and Si≡O in the silicon oxide exist in different proportions depending the film-growing temperature.

Subsequently, it will be described how to analyze different infrared absorption spectra for a thin-film growing temperature. An analytical technique based on pattern recognition using PLS regression is used in this embodiment for the analyzing of different infrared absorption spectra for a film-growing temperature.

Figure 3A:
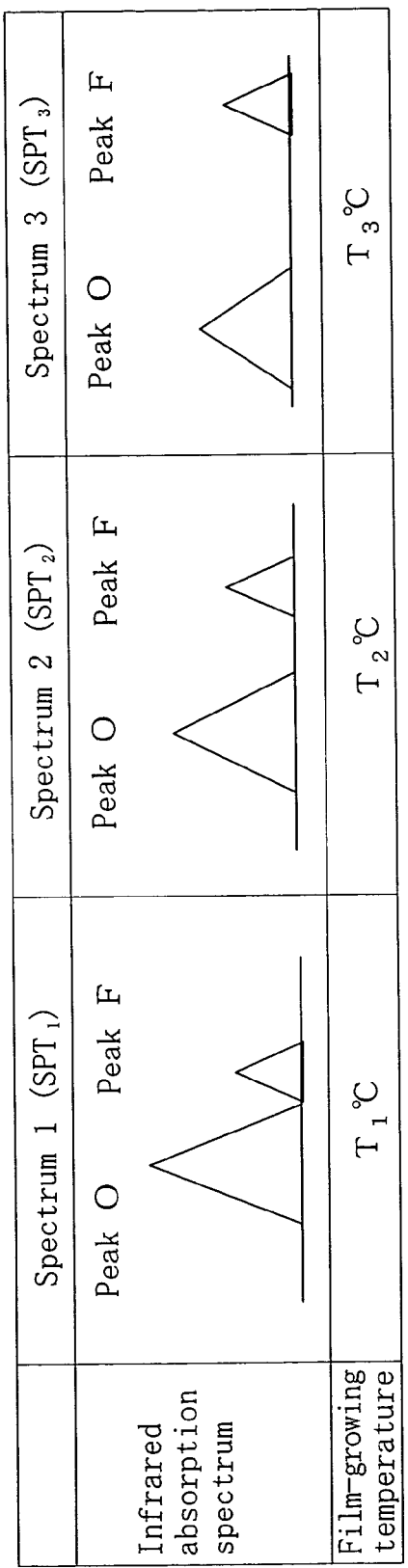
FIGS. 3(a) through 3(c) are respectively views illustrating reference infrared-absorption spectra, and the infrared absorption spectrum of a film targeted for measurement, and a view indicating a method for determining a film-growing temperature using PLS regression.
Figure 3C:
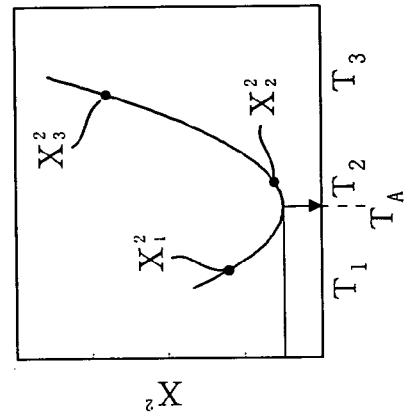
Figure 3B:
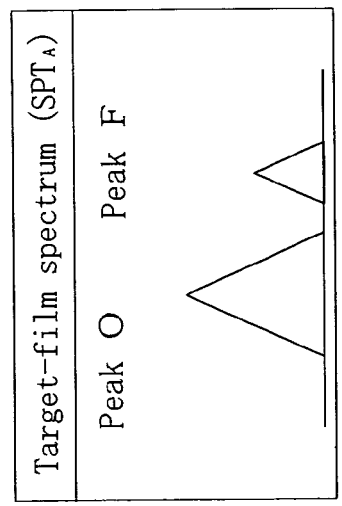

FIGS. 3(a) and 3(b) are views illustrating reference infrared-absorption spectra, and the infrared absorption spectrum of a film targeted for measurement (which will be referred to as a "target-film infrared absorption spectrum",) in an analytical model of multivariate analysis technology based on pattern recognition, and FIG. 3(c) is a view indicating a method for determining a film-growing temperature using PLS regression. In FIGS. 3(a) and 3(b), peaks O indicate peaks of absorption by, e.g., $SiO_2$, and peaks F indicate peaks of absorption by SiF. As shown in the figures, distance between the peaks O and the associated peaks P change depending on the film-growing temperature.

First, as shown in FIG. 3(a), the reference infrared-absorption spectrum patterns, $SPT_1$, $SPT_2$, and $SPT_3$ of multiple FSG films (three films in this embodiment) that have been formed at mutually different film-growing temperatures (T1<T2<T3) are previously measured using FT-IR spectroscopy and stored as a database in a storage device.

A target-film infrared-absorption spectrum pattern $SPT_A$ is then measured as shown in FIG. 3(b).

Figure 4A:
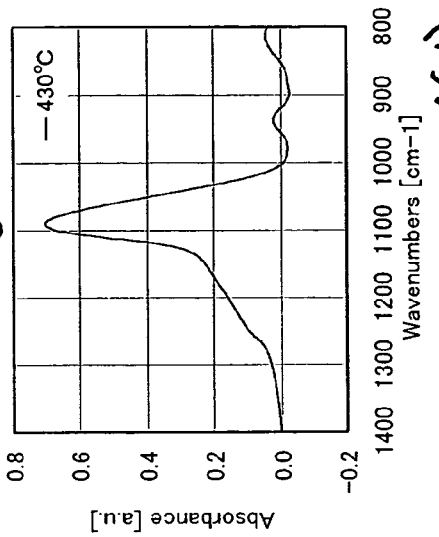
FIGS. 4(a) through 4(d) respectively show the infrared absorption spectra of FSG films that have been grown at 380° C., 430° C. and 480° C., and the infrared absorption spectrum of an FSG film targeted for measurement.
Figure 4B:
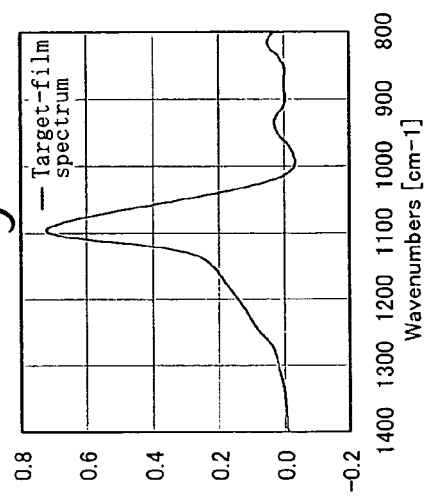
Figure 4C:
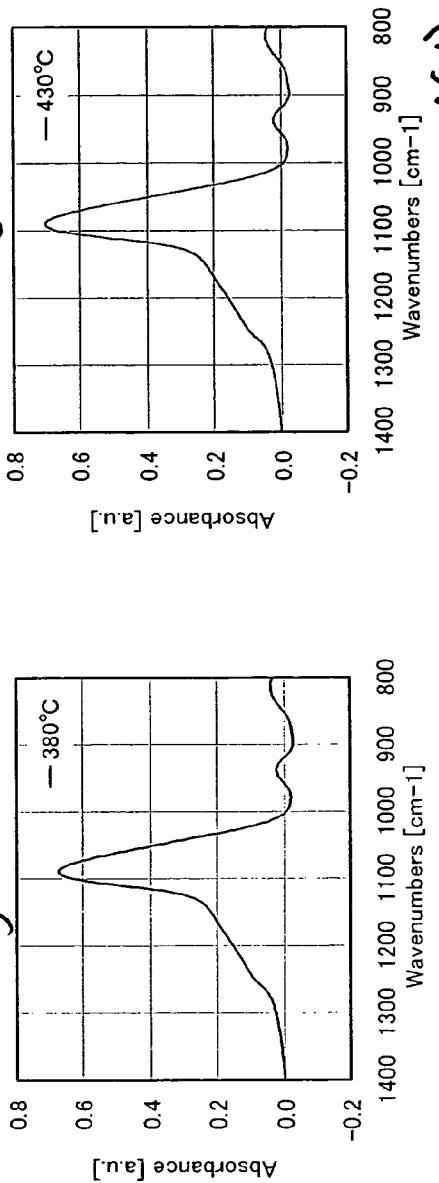
Figure 4D:
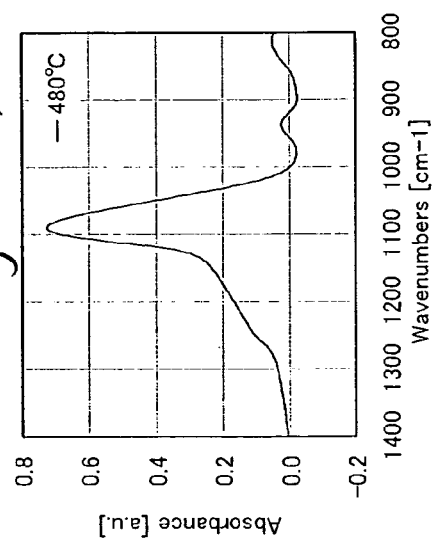

FIGS. 4(a) through 4(d) respectively show the infrared absorption spectra of FSG films that have been grown at 380° C., 430° C. and 480° C., and the infrared absorption spectrum of an FSG film targeted for measurement. Specifically, FIGS. 4(a) through 4(c) show specific examples of the infrared-absorption spectrum patterns $SPT_1$, $SPT_2$ and $SPT_3$, shown in FIG. 3(a), for the three FSG films that have been grown at mutually different temperatures. FIG. 4(d) shows a specific example of the target-film infrared-absorption spectrum pattern $SPT_A$ shown in FIG. 3(b).

Subsequently, pattern analysis is carried out to obtain a value $X_i^2$ by the following equation (1), the value $X_i^2$ being the sum of squares of the difference between each of the three reference infrared-absorption spectrum patterns $SPT_1$, $SPT_2$, and $SPT_3$, and the target-film infrared-absorption spectrum pattern $SPT_A$.

$$X_i^2 = \Sigma(SPT_i - SPT_A)^2 \qquad (1)$$

In $\Sigma(SPT_i - SPT_A)^2$ on the right side of the equation (1), the difference in absorption, at each wavelength, between each reference infrared-absorption spectrum pattern and the target-film infrared-absorption spectrum pattern, is squared and integrated for each wavelength. That is, from the right side of the equation (1), the sum of squares of the differences is obtained. The value $X_i^2$ in the equation (1) includes a pattern deviation resulting from, e.g., the difference in maximum absorption value at the peak, and in wavelength indicating the maximum absorption value, between each reference infrared-absorption spectrum pattern and the target-film infrared-absorption spectrum pattern, and from the difference in the distance between each peak O and its associated peak F shown in FIG. 3(a).

Consequently, as shown in FIG. 3(c), three points $X_1^2$, $X_2^2$ and $X_3^2$ representing the sums of squares of the differences are obtained, thereby determining a curve $L_A$ (a quadratic curve in this example for the sake of simplicity) that passes through the three points $X_1^2$, $X_2^2$ and $X_3^2$. From this curve $L_A$, a temperature $T_A$ at which the sum of squares of the differences $X^2$ becomes the minimum, is found. This temperature is estimated as the film-growing temperature of the FSG film. The following describes a specific example of this procedure.

FIGS. 12(a) and 12(b) are respectively tables showing exemplary settings in a constructed database and a calculation result. In a PLS regression solution technique, a solution is obtained by a numerical computation technique using a computer, and the parameters are adjusted so that the correct coefficient for the temperature in the database when multiple regression analysis is performed based on PLS regression, with respect to the PLS model of the database, is close to 1.0. According to the results of numerical computation performed by the present inventors on this occasion, when an infrared absorption spectrum in the range from a maximum wavenumber of 1600 $cm^{-1}$ to a minimum wavenumber of 700 $cm^{-1}$ is used, and the number of divisions for the infrared absorption spectrum is set to 467, the resultant correct coefficient is highest, yielding a 0.98 correct coefficient.

FIG. 13 is a table showing the results of examination of temperatures in the constructed database and analysis temperatures. Shown in FIG. 13 are temperatures in the database (corresponding to the film-growing temperatures Ti associated with the spectrum patterns $SPT_i$ shown in FIG. 3(a)); analysis temperatures (corresponding to the film-growing temperature $T_A$ shown in FIG. 3(c)); differences (difference between the temperature in the database and the analysis temperature); error rates (obtained by multiplying by 100 the quotient obtained by diving the difference with the associated temperature in the database); spectral residuals (corresponding to $X^2$ in FIG. 3(c)); and reliability of the analysis values.

In FIG. 13, it is more preferable that the spectral residuals and the reliability of the analysis values be as small as possible, and in which case, the reliability of the analysis temperatures heightens. As shown in the figure, the values indicating the spectral residuals and the reliability of the analysis temperatures, are sufficiently small with respect to the setting temperatures in the database, and thus can be judged to present no practical problem. Further, the results of the examinations using the database prepared on this occasion show that the error rates for the FSG-film growing temperatures are not more than ±1.0%. Specifically, a PLS model that allows temperatures in the range extending from 384.2° C. to 504.5° C. to be estimated within ±1.0% accuracy, is obtained from the calculation results.

Second Embodiment

For easy understanding, a method for estimating, as a parameter, film-growing temperature alone is described in the foregoing example. However, thin films formed in the actual process do not have constant thickness and constant impurity concentration (e.g., fluorine concentration), for example, such that there are variances in these parameters between wafers or in a wafer. The thickness or impurity-concentration variance may cause deterioration in the accuracy of film-growing temperature estimation. In the actual process, it is thus necessary to perform multivariate analysis using parameters including, e.g., thickness and impurity concentration even if the purpose is to estimate film-growing temperature.

Next, it will be described how to estimate various parameters including not only the film-growing temperature of a thin film but also the quality and thickness thereof. In the following description, the infrared-absorption spectrum patterns of FSG films that have been grown in an HDP-CVD apparatus are used as an example.

Figure 5:
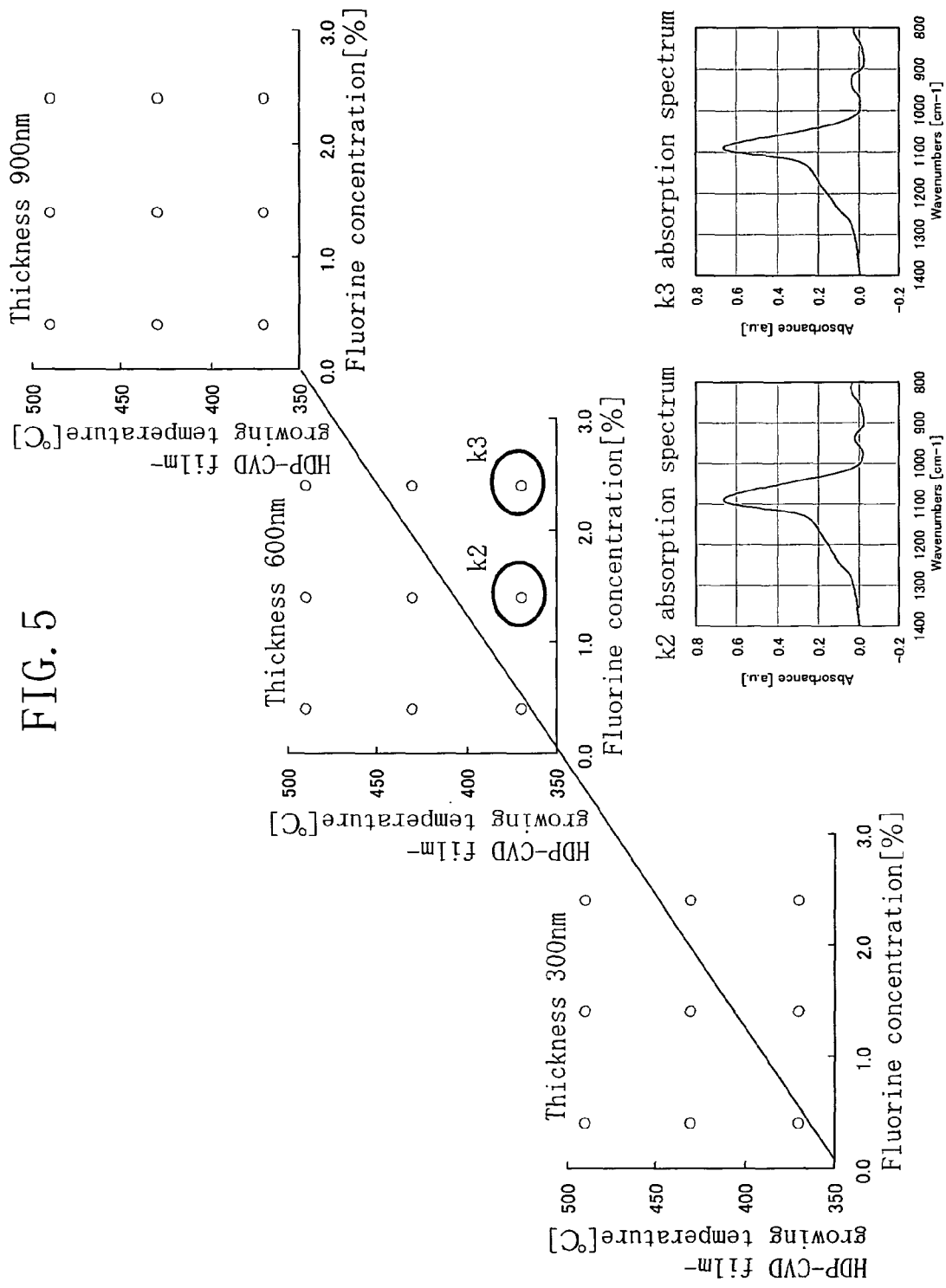
FIG. 5 shows how to construct a database from the infrared-absorption spectrum patterns of FSG films.

FIG. 5 shows how to construct a database from the infrared-absorption spectrum patterns of FSG films. Prepared first are matrixes in which film-growing conditions are expressed. The film-growing conditions, which determine FSG-film quality, include film-growing temperature in an HDP-CVD apparatus, fluorine concentration in FSG films, and the thicknesses of the FSG films. For each of these condition categories, a plurality of conditions (three conditions, for example) are established in the matrixes. FSG films are grown in accordance with all conditions in the matrixes, and the infrared absorption spectra of the films are measured by FT-IR spectroscopy, thereby constructing a database from the infrared-absorption spectrum patterns.

In the example shown in FIG. 5, twenty-seven infrared-absorption spectrum patterns in total are complied into the database with respect to the three different thicknesses 300 nm, 600 nm and 900 nm, the three different film-growing temperatures 370° C., 430° C. and 490° C., and the three different fluorine concentrations 0.4%, 1.4% and 2.4%. Also illustrated in the figure are the infrared-absorption spectrum patterns of the films obtained under respective conditions k2 and k3 in which the thickness of each film is 600 nm, the film-growing temperature of each film is about 370° C., while the fluorine concentrations are respectively about 1.4% and about 2.4%.

Subsequently, the thickness, film-growing temperature and fluorine concentration of a target film for measurement are computed from the infrared-absorption spectrum pattern that the target film shows, using the various parameters in the database shown in FIG. 5. In the computation process, multivariate analysis is performed by a procedure as is shown in FIGS. 3(a) and 3(b), thereby finally obtaining in a multi-dimensional space numerous points $X_i^2$ such as shown in FIG. 3(c), each indicating a sum of squares of differences. In this case, since multi-dimensional analysis has to be carried out, results of the analysis cannot be presented in graphical form such as is shown in FIG. 3(c). A multi-dimensional figure that is most likely to pass through these numerous points $X_i^2$ is then obtained. The film thickness, film-growing temperature and fluorine concentration at the point indicating the minimum value in this multi-dimensional figure are computed as the thickness, film-growing temperature and fluorine concentration of the target film.

Instead of the above-mentioned estimation method, three graphs in which the abscissas represent the film-growing temperature, thickness and fluorine concentration, respectively, may be prepared, and in the graphs, a location X on the abscissa, which represents the minimum value on a quadratic curve passing through numerous points $X_i^2$, may be approximated to the film-growing temperature, thickness or fluorine concentration of the target film.

As has been mentioned above, a solution model of a multivariate analysis technique based on pattern recognition can be used to infer which infrared-absorption spectrum pattern in the constructed database is closest to the infrared-absorption spectrum pattern of the target film, thereby obtaining the film-growing temperature, fluorine concentration and thickness thereof, using the multivariate analysis technique.

Figure 6:
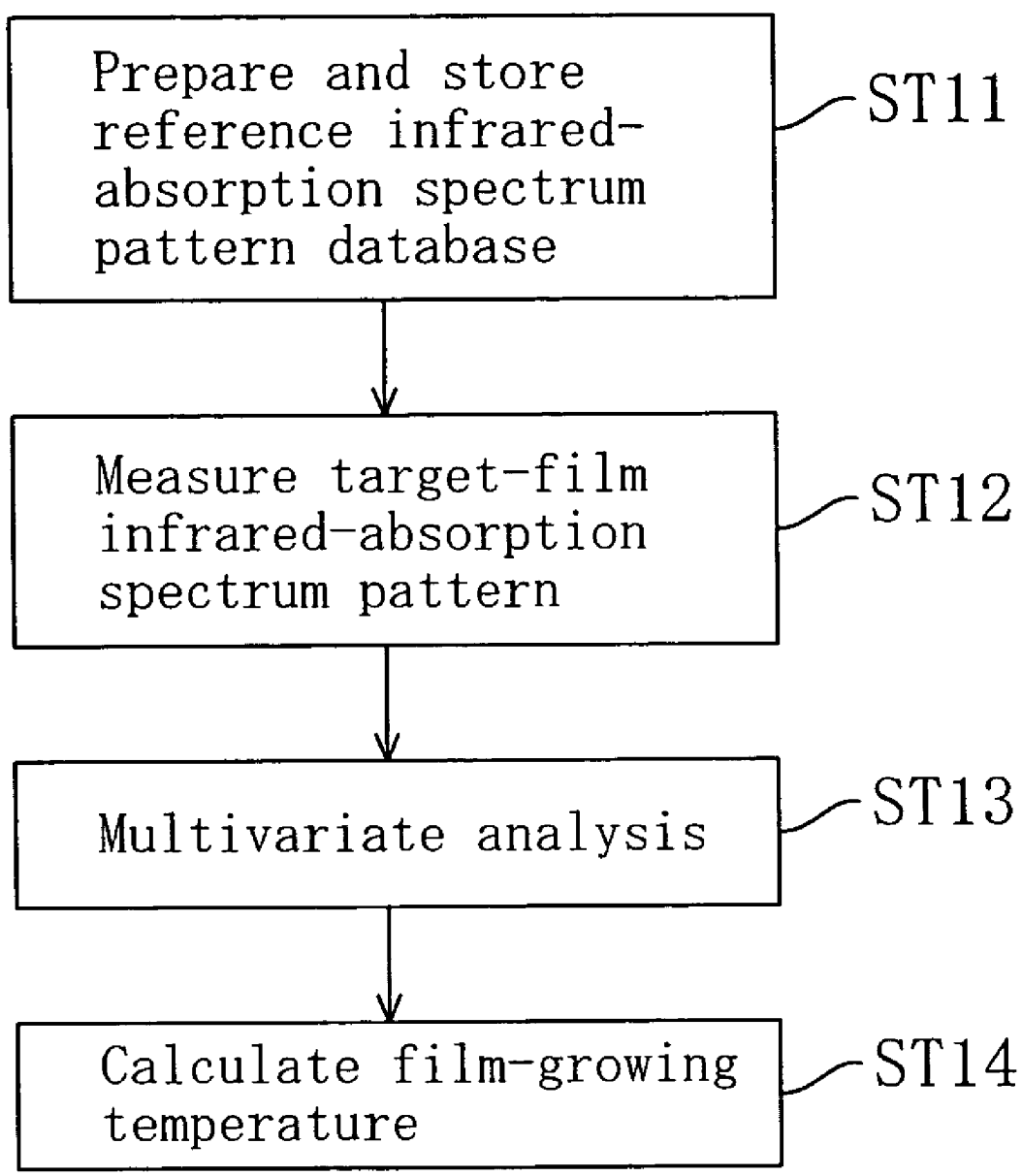
FIG. 6 is a flow chart showing a procedure for inferring the film-growing temperature of a target film (FSG film) by multivariate analysis.

FIG. 6 is a flow chart showing a procedure for inferring, by multivariate analysis, the film-growing temperature of a target film (FSG film) for measurement.

First, in step ST11, reference infrared-absorption spectrum patterns (for example, patterns with respect to the twenty-seven kinds of conditions shown in FIG. 6) are prepared and stored as a database in a storage device.

Next, in step ST12, the infrared-absorption spectrum pattern of the target film is measured using FT-IR spectroscopy. In should be understood that a method other than FT-IR spectroscopy may be used for the measurement of the infrared-absorption spectrum patterns in the present invention.

Then, in step ST13, multivariate analysis is performed. Obtained in the example shown in FIGS. 2(a) through 2(c) is the value $X_i^2$ that corresponds to the sum of squares of the difference between each of the three reference infrared-absorption spectrum patterns $SPT_1$, $SPT_2$, and $SPT_3$, and the infrared-absorption spectrum pattern $SPT_A$ of the target film. On the other hand, performed in this embodiment is analysis (multivariate analysis) in which the difference in absorption value, at each wavelength, between each of the twenty-seven reference infrared-absorption spectrum patterns and the target-film infrared-absorption spectrum pattern, is squared and integrated for each wavelength.

Subsequently, in step ST14, the film-growing temperature and other factors are computed based on the pattern analysis results. In the first embodiment, the temperature $T_A$ at which the sum of squares of the differences $X^2$ becomes the minimum is obtained from the curve $L_A$ that passes through the three points $X_1^2$, $X_2^2$ and $X_3^2$ shown in FIG. 3(c), and this temperature is computed as the film-growing temperature of the FSG film. In this embodiment, however, the twenty-seven points $X_i^2$ that represent the sums of squares of the differences like the points shown in FIG. 3(c), are obtained in a multi-dimensional space, such that a multi-dimensional figure which is most likely to pass through the points $X_i^2$ is obtained. The film-growing temperature at the point indicating the minimum value in the multi-dimensional figure is computed as the film-growing temperature of the target film.

Figure 7:
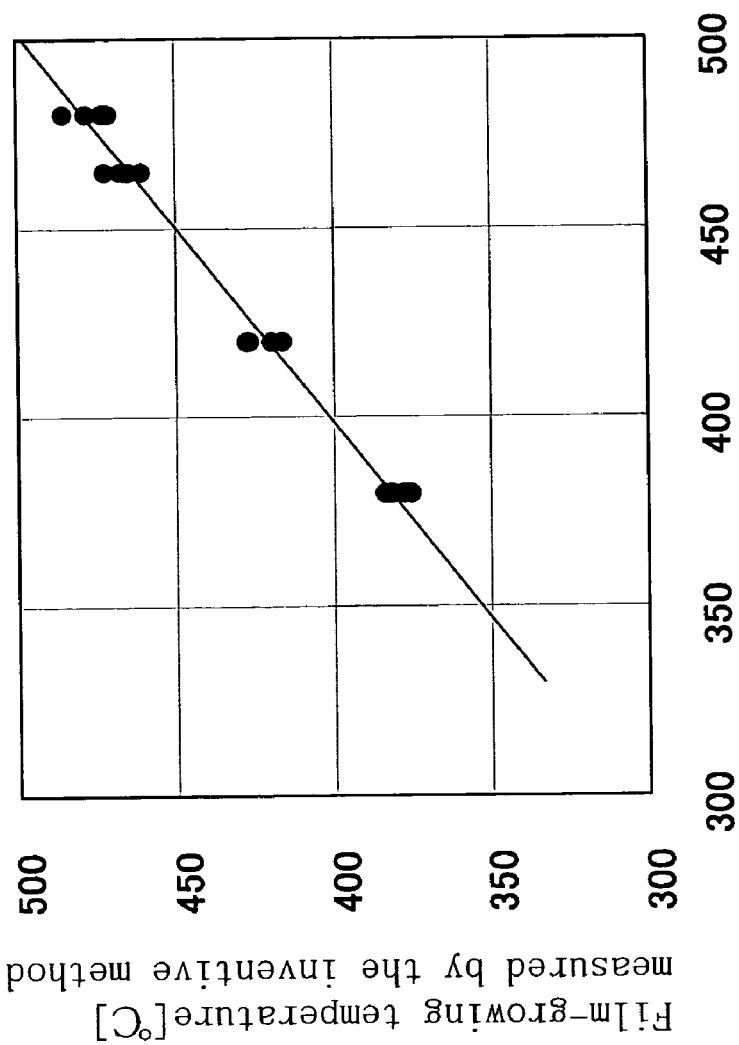
FIG. 7 is a graph showing correlation between film-growing temperatures in an HDP-CVD apparatus that are inferred by a method according to a second embodiment, and film-growing temperatures measured by a method based on a known method.

FIG. 7 is a graph showing correlation between film-growing temperatures in an HDP-CVD apparatus that are inferred by the method of this embodiment, and film-growing temperatures measured by a method based on the technique described in International Publication No. WO99/57146. Considering that with the method described in International Publication No. WO99/57146, in the case of temperatures at or below 500° C., it is difficult to determine the rate at which an amorphous layer is recovered, the other method based on the described technique is used. As shown in FIG. 7, the film-growing temperatures in the present invention and the film-growing temperatures obtained by applying the known method have a correlation of almost 1:1. This correlation shows that the results of the measurement, by FT-IR spectroscopy, of the film-growing temperatures in the HDP-CVD are good.

In accordance with this embodiment, the film-growing temperature of a thin film can be measured accurately by performing multivariate analysis using, as parameters, for example, the thin film's thickness, impurity concentration and film-growing temperature obtained by FT-IR spectroscopy. In particular, as described above, with the technique described in International Publication No. WO99/57146, it is difficult to measure film-growing temperatures at or below 500° C. In contrast, film-growing temperatures at or below 500° C. can be measured by the method of the present invention, and in addition, the measurements are performed easily and quickly (specifically, in a few minutes) by the inventive method.

It should be noted, however, that the range of film-growing temperatures measurable by the temperature measuring method of the present invention is not limited by 500° C. or less. The range of film-growing temperatures measurable by the inventive method includes substantially the same range for the technique described in International Publication No. WO99/57146, and further includes lower temperature ranges. In recent years, as the semiconductor fabrication process has been performed at lower temperatures, the present invention particularly can exhibit the remarkable effect of being able to measure temperatures in the 350° C.-to-500° C. process-temperature range, which is the range in which the semiconductor-device wiring process is carried out.

Moreover, in the inventive method, the temperature at which a film has been grown can be easily measured by performing in-line monitoring of the infrared absorption spectrum while a film-growing apparatus is used under the same conditions as in the process, thus enabling the film-growing temperatures in all film-growing processes to be measured without causing any deterioration in productivity.

Third Embodiment

As an exemplary application of the thin-film evaluation method of the present invention, it will be described how to fabricate semiconductor devices on production lines.

Figure 8:
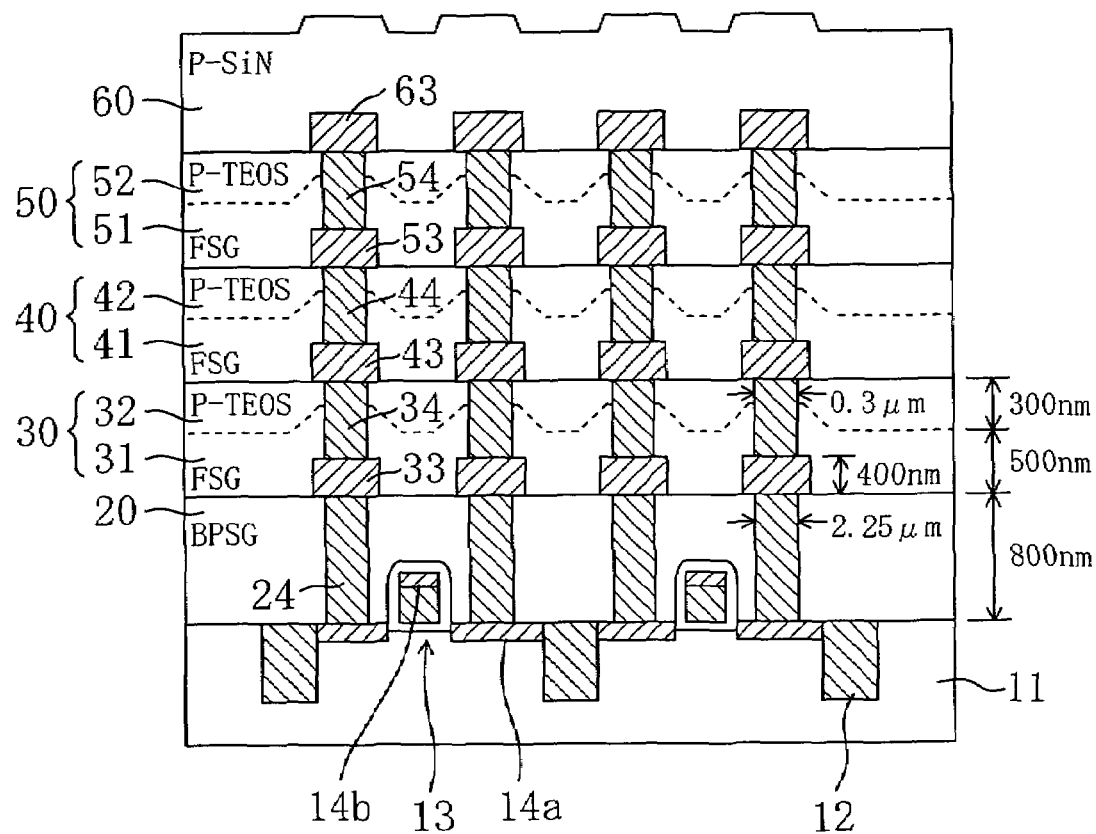
FIG. 8 is a cross sectional view showing the structure of a semiconductor device formed in a third embodiment.

FIG. 8 is a cross sectional view showing the structure of a semiconductor device formed in a third embodiment. A trench isolation region 12 which defines an active region is formed in a silicon substrate 11. Many MISFETs 13 are formed in the active region surrounded with the trench isolation region 12. Formed on the respective upper portions of a source/drain region (not shown) and a gate electrode of each MISFET 13 are silicide layers 14a and 14b formed by a salicide process.

In the fabrication method of this embodiment, a first interlevel dielectric film 20 of a BPSG film is first deposited on the silicon substrate 11 on which the numerous MISFETs 13 have been formed. The first interlevel dielectric film 20 has a thickness of about 800 nm.

Formed next are contact holes which go through the first interlevel dielectric film 20 to reach the associated silicide layers 14a and 14b of the source/drain regions and the gate electrodes. The contact holes are then filled with tungsten (W), thereby forming plugs 24. Although plugs on the gate electrodes are not shown in FIG. 8, the plugs that are connected to the gate electrodes appear in a cross section other than the cross section shown in FIG. 8. Each plug 24 has a diameter of about 0.25 $\mu$m.

Next, an Al film is deposited on the first interlevel dielectric film 20 and then patterned, thereby forming Al interconnects 33 (first-layer interconnects) that are connected to the plugs. The thickness of the Al interconnects 33 is about 400 nm. Thereafter, a second interlevel dielectric film 30 is deposited on both the first interlevel dielectric film 20 and the Al interconnects 33. The second interlevel dielectric film 30 includes a lower film 31 of an FSG film and an upper film 32 of a P-TEOS film (plasma TEOS film). The thicknesses of the lower film 31 and the upper film 32 are about 500 nm and about 300 nm, respectively.

Now, in the present invention, before the lower film 31 of the second interlevel dielectric film 30 is deposited, a region to be measured (measuring region) in the wafer is irradiated with an infrared beam in order to measure the infrared absorption spectrum of the entire substrate underlying the lower film 31. The lower film 31 is then deposited by an HDP-CVD process. The lower film 31 of an FSG film is grown under the conditions that the pressure inside a chamber of a film-growing apparatus is 6 mTorr (about 0.8 Pa); the RF power of a plasma CVD apparatus is 900W/2300W; the bias power is 2350W; the He pressure on the bottom face of the wafer is 2 mTorr (about 0.27 Pa) on the IN side; the TOP flow rate of argon gas is 9 (ml/min); the SIDE flow rate of the argon gas is 46 (ml/min); the TOP flow rate of oxygen is 53 (ml/min); the SIDE flow rate of the oxygen is 73 (ml/min); the TOP flow rate of silane is 4 (ml/min); the SIDE flow rate of the silane is 40 (ml/min); and the TOP flow rate of silicon tetrafluoride is 28 ml/min.

After the lower film 31 is deposited, the measuring region of the wafer is irradiated with infrared radiation in order to measure the infrared absorption spectrum. From the difference between both infrared absorption spectra, the infrared absorption spectrum of the lower film 31 alone is measured. Further, using the reference infrared-absorption spectrum patterns described in the second embodiment (see FIG. 5), multivariate analysis of the infrared-absorption spectrum pattern of the lower film 31 is performed using the film-growing temperature, film thickness and fluorine concentration as parameters. In this manner, the film-growing temperature, thickness and fluorine concentration of the lower film 31 are measured to determine whether the conditions for the deposition of the lower film 31 are appropriate or not.

Subsequently, after the upper film 32 of the second interlevel dielectric film 30 is deposited, via holes are formed in the second interlevel dielectric film 30 so as to reach the Al interconnects 33 on the first interlevel dielectric film 20. The via holes are then filled with tungsten (W), thereby forming plugs 34. The upper film 32 of the second interlevel dielectric film 30 has a thickness of about 300 nm, and the plugs 34 have a diameter of about 0.3 $\mu$m.

Thereafter, Al interconnects 43 (second-layer interconnects) and a third interlevel dielectric film 40 are formed on the second interlevel dielectric film 30 by the same procedure as described above. The third interlevel dielectric film 40 includes a lower film 41 of an FSG film and an upper film 42 of a P-TEOS film. When the lower film 41 is formed, multivariate analysis using the infrared absorption spectra is performed in order to control the film-growing temperature, film thickness and fluorine concentration, for example.

Al interconnects 53 (third-layer interconnects) and a forth interlevel dielectric film 50 are then formed on the third interlevel dielectric film 40 by the same procedure as described above. The fourth interlevel dielectric film 50 includes a lower film 51 of an FSG film and an upper film 52 of a P-TEOS film. When the lower film 51 is formed, multivariate analysis using the infrared absorption spectra is performed in order to control the film-growing temperature, film thickness and fluorine concentration, for example.

Al interconnects 63 (fourth-layer interconnects) and a passivation film 60 of a P—SiN film are then formed on the forth interlevel dielectric film 50.

In this embodiment, multivariate analysis utilizing infrared absorption spectra is not performed to measure the film-growing temperatures of the first interlevel dielectric film 20 of a BPSG film, the respective upper films 32, 42 and 52 of the second through fourth interlevel dielectric films of a P-TEOS film, and the passivation film 60 of a P—SiN film. The reason for this is as follows. Used for BPSG films, P-TEOS films and P—SiN films is not an HDP-CVD apparatus using high-density plasma, but a CVD apparatus utilizing normal plasma or thermal reaction, which does not have a mechanism, such as found in an HDP-CVD apparatus, in which an electrostatic chuck is employed to hold the wafer and the reverse face of the wafer is cleaned with He. This structure allows a thermocouple to be embedded in a lower electrode in a conventional plasma CVD apparatus in order to measure the temperature of the lower electrode, for example, thereby indirectly measuring the wafer temperature. Note that if multivariate analysis based on infrared absorption spectra is performed when films, such as BPSG films, P-TEOS films and P—SiN films, are formed, impurity concentration (e.g., boron or phosphorous concentration in a BPSG film) and film thickness can also be measured, enabling process steps to be strictly controlled.

Also, the trench isolation region 12 may be made of USG (undoped silicate glass) deposited using an HDP-CVD apparatus, and thus multivariate analysis based on infrared absorption spectra may also be performed for the trench isolation region 12.

Figure 9:
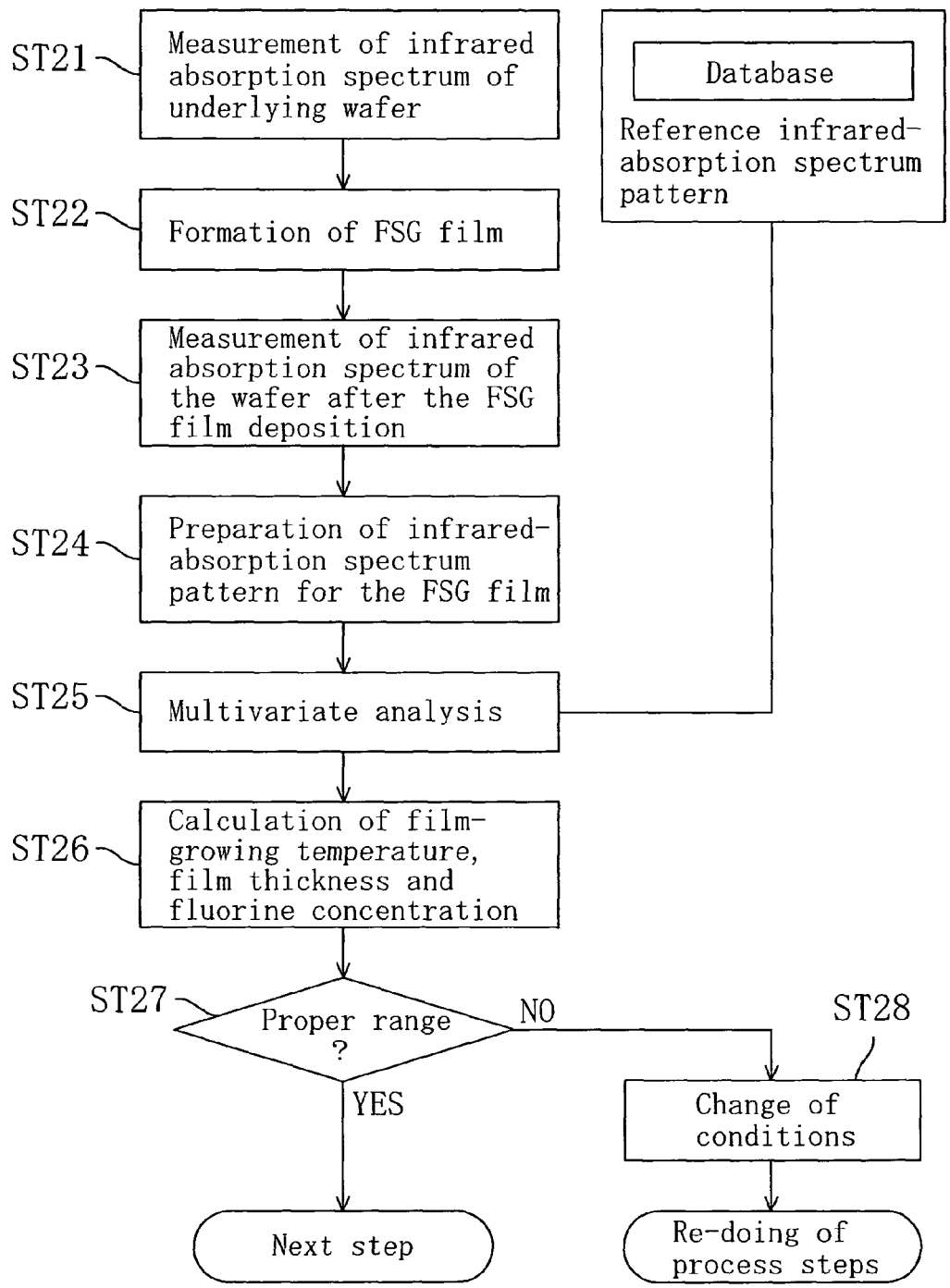
FIG. 9 is a flow chart illustrating process steps before and after an FSG film is formed in the fabrication procedure of the third embodiment.

FIG. 9 is a flow chart illustrating process steps before and after an FSG film is formed in the fabrication procedure of this embodiment.

First, in step ST21, the infrared absorption spectrum of an underlying wafer is measured. In the case of forming the lower film 31 of the second interlevel dielectric film 30, the underlying wafer corresponds to the wafer on which the first interlevel dielectric film 20 and the plugs 24 have already been formed. In the case of forming the lower film 41 of the third interlevel dielectric film 40, the underlying wafer corresponds to the wafer on which the second interlevel dielectric film 30 and the plugs 34 have already been formed. In the case of forming the lower film 51 of the fourth interlevel dielectric film 50, the underlying wafer corresponds to the wafer on which the third interlevel dielectric film 40 and the plugs 44 have already been formed.

Next, in step ST22, an FSG film (which in this embodiment is each of the lower films 31, 41 and 51) is deposited using an HDP-CVD apparatus under the above mentioned conditions.

The infrared absorption spectrum of the wafer after the FSG film has been deposited is then measured in step ST23. That is, the absorption spectrum for infrared radiation that is transmitted through both the FSG film and the underlying wafer, is measured.

Subsequently, in step ST24, the difference between the infrared absorption spectra measured in steps ST23 and ST21 is computed wavelength by wavelength, thereby preparing the infrared-absorption spectrum pattern of the FSG film alone.

Then, in step ST25, multivariate analysis is carried out in accordance with the method described in the second embodiment, using reference infrared-absorption spectrum patterns (for example, numerous spectrum patterns in which film-growing temperature, film thickness and fluorine concentration such as shown in FIG. 5 are used as parameters) pre-stored in a database. As a consequence, a graph or a function that replaces the curve shown in FIG. 3(c) with a multi-dimensional figure or multi-dimensional function, is obtained.

In step ST26, from the multi-dimensional figure or multi-dimensional function obtained in step ST25, the film-growing temperature, film thickness and fluorine concentration, e.g., of the FSG film that give the minimum value in the multi-dimensional figure or function, are inferred.

Thereafter, in step ST27, it is determined whether the film-growing temperature, film thickness and fluorine concentration inferred in step ST26 are within proper range or not. If the film-growing temperature is too low, the contact (specifically the contact resistance) between the plugs formed in the interlevel dielectric film located under the FSG film, and the conductor layer in contact with and located under the plugs, may deteriorate. An excessively low film-growing temperature may also cause the following drawbacks.

Figure 10:
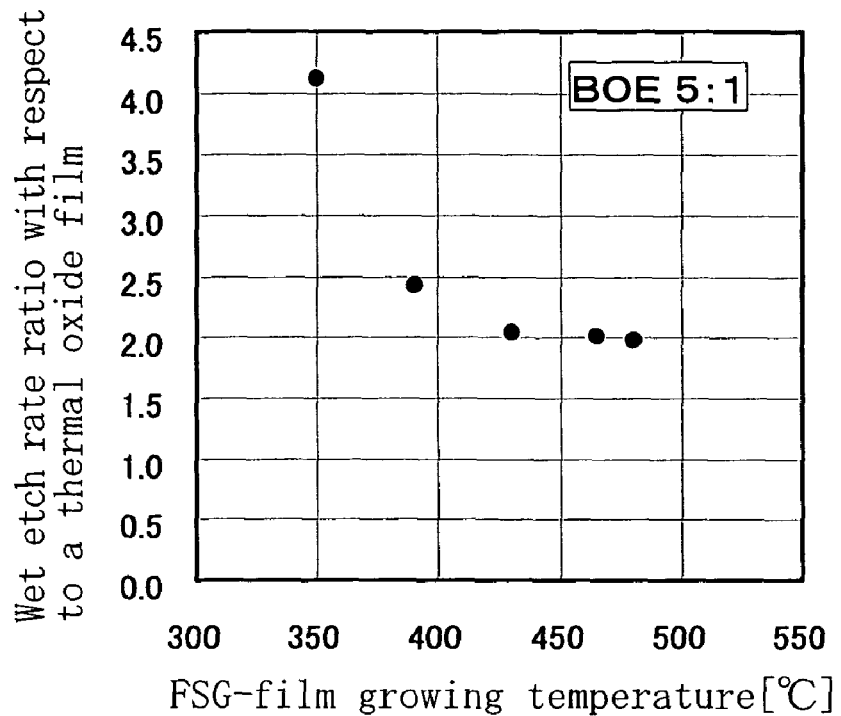
FIG. 10 shows the dependency of FSG-film etch rate on film-growing temperature.

FIG. 10 shows the dependency of FSG-film etch rate on film-growing temperature. In FIG. 10, the ordinate represents the etch rate as a ratio to the etch rate of a thermal oxide film. As shown in FIG. 10, an excessively low film-growing temperature results in a high etch rate, leading to difficulty in controlling, e.g., etch time in the process steps. Specifically, when the etch rate of a thin film increases, drawbacks such as overetching may be caused.

More specifically, as the quality of an FSG film, e.g., the etch rate may be included in the parameters for multivariate analysis.

On the other hand, an excessively high film-growing temperature may cause deterioration in the characteristics of the Al film that has been formed in the lower portion of the FSG film. In view of this, the FSG-film growing temperature has an appropriate range. In this example, the FSG-film growing temperature is preferably within the range between 380° C. or more and 480° C. or less. Further, if the film thickness is too large, the formation of the via holes and the filling of the plugs become difficult, while if the film thickness is too small, capacity between interconnects sandwiching an interlevel dielectric film may increase, or the insulating property of the interlevel dielectric film may deteriorate. The film thickness therefore also has a proper range. Furthermore, an excessively low fluorine concentration may lead to an insufficiently reduced relative dielectric constant of the interlevel dielectric film, while an excessively high fluorine concentration may cause the Al film to be peeled off due to F diffusion. In view of this, the fluorine concentration also has an appropriate range.

As a result, when the film-growing temperature, film thickness, and fluorine concentration, for example, fall within their respective proper ranges, it is possible to directly proceed to the next step. On the other hand, if the film-growing temperature, film thickness, and fluorine concentration, for example, fall outside their respective proper ranges, it is necessary to go to step ST27, wherein after the conditions in the HDP-CVD are changed, the FSG film is etched away for deposition of another FSG film.

It should be understood that after the conditions are changed in step ST27, it is possible to proceed to the next step. Even in that case, when the lower film 41 of the third interlevel dielectric film 40 is formed after the lower film 31 of the second interlevel dielectric film 30 has been formed, the FSG film can be deposited under the appropriate conditions.

As has been described above, parameters such as the film-growing temperature, film thickness and fluorine concentration of FSG films are easily maintained in their respective proper ranges in the semiconductor device fabrication process, enabling strict and easy control of the semiconductor device fabrication process. Moreover, yields can be improved by re-doing formation of a thin film.

Note that the infrared absorption spectra measured by FT-IR spectroscopy shown in FIG. 1 are the data of the infrared absorption spectra of the FSG films alone that have been grown in an HDP-CVD apparatus. However, it has been confirmed that with the combined infrared absorption spectrum of an FSG film and a silicon substrate, the film-growing temperature in an HDP-CVD apparatus can be measured as in the case shown in FIG. 7.

In addition, according to the inventive method, since the infrared-absorption spectrum components of a thin film alone can be measured by performing difference computation, not only in-line monitoring is available, but also the film-growing temperature of an actual device, in which the reverse face of a substrate has a complicated structure, can be measured accurately.

Moreover, although FSG films grown in an HDP-CVD apparatus are used in the descriptions in the foregoing embodiments, the present invention is also applicable to cases of growing other silicon oxide films, such as a phosphorous-doped silicon oxide film (PSG film), a boron/ phosphorous-doped silicon oxide film (BPSG film), and a silicon nitride film. Additionally, in the descriptions of the foregoing embodiments, an HDP-CVD apparatus is used to grow silicon oxide films such as FSG films. The present invention is, however, applicable to cases in which other film growing apparatuses, such as a conventional plasma CVD apparatus (P-CVD) and a low pressure CVD apparatus (LP-CVD), are used to grow films.

Fourth Embodiment

In this embodiment, it will be described how to utilize measurement of a film-growing temperature in order to measure temperature inside a chamber.

As has been described above, since the infrared absorption spectrum of, e.g., an FSG film can be used to measure the film-growing temperature, chamber temperature can also be measured. Once the chamber temperature is known, the temperature can be used not only for CVD, but also for each process in the semiconductor device fabrication procedure.

Conventionally, temperature inside a chamber has been measured with a temperature sensor attached to the bottom face of a thermocouple-equipped wafer. Although the use of the thermocouple-equipped wafer allows the temperature of the reverse face of the wafer to be measured, the temperature of the wafer surface, that is, the actual temperature at which the amorphous region is subjected to an annealing process, cannot be measured. In addition, the measurable temperature range is limited and thus measurements of temperatures higher than a certain level become difficult.

Also, with the technology described in International Publication No. WO99/57146, for temperatures at or below 500° C., the rate at which a layer is recovered from the amorphous state is unknown. This is because at low temperatures, recovery from the amorphous state completes at a very early stage and would not proceed even if further time elapsed.

In contrast, the inventive method using infrared absorption spectra has the advantage of being able to measure any temperatures that fall within the temperature range in which CVD is possible. In particular, the present invention is highly effective in the case of temperatures at or below 500° C., measurements of which are difficult with the technology described in International Publication No. WO99/57146.

Figure 11:
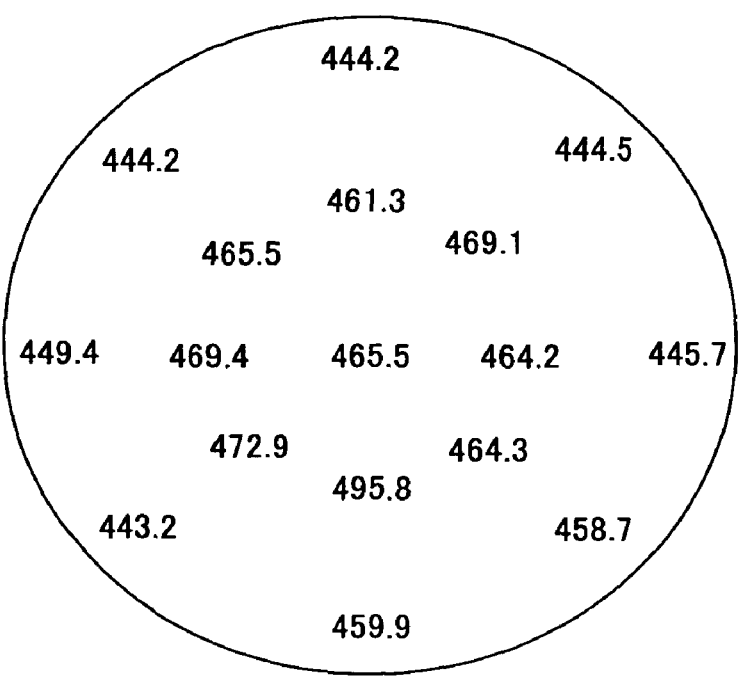
FIG. 11 shows data illustrating temperature distribution in a wafer face, obtained for an FSG film that has been formed using an HDP-CVD apparatus.

FIG. 11 shows data illustrating temperature distribution in a wafer face, obtained for an FSG film that has been formed using an HDP-CVD apparatus. Since the diameter of the infrared beam is about 5 mm, infrared absorption spectra can be measured with respect to a number of spots in the wafer. In that case, the spots in the wafer with respect to which infrared absorption spectra have been measured before the film is formed, have to substantially agree with the spots in the wafer with respect to which infrared absorption spectra are measured after the film has been formed. In this respect, since currently used infrared radiation measuring devices have very improved positioning accuracy, there have been practically no problems.

As shown in FIG. 11, the temperature distribution in the wafer face can be measured by performing multivariate analysis utilizing infrared absorption spectra in accordance with the present invention. Based on this, temperature distribution in a chamber of a CVD apparatus may be measured. The wafer used for the temperature measurement may be a product wafer on a production line or a control wafer used for procedure control.

Other Embodiments

In the foregoing embodiments, target films for measurement are irradiated with infrared radiation in order to measure the infrared absorption spectra using FT-IR spectroscopy, thereby evaluating the target films. The present invention is, however, applicable to cases in which other spectroscopic techniques, such as dispersive infrared spectroscopy, laser Raman spectroscopy or X-ray photoelectron spectroscopy, are used to measure an absorption spectrum for observing bonds between the atoms forming a thin film.

According to the present invention, the growing temperatures or characteristics of films can be measured by in-line monitoring of the film-growing apparatus, thereby enabling the film growing temperatures in all film-growing processes to be measured without causing any deterioration in productivity.

INDUSTRIAL APPLICABILITY

The present invention is applicable to fabrication of various kinds of transistors and semiconductor memories and other semiconductor devices that are incorporated into electronic equipment.

The invention claimed is:

1. A film evaluation method comprising the steps of:
(a) irradiating with electromagnetic waves a substrate on which a film is formed, thereby measuring an absorption spectrum for the electromagnetic waves, and
(b) calculating from the shape of the absorption spectrum a specific value corresponding to the quality of the film,
wherein in step (b), the specific value is calculated from a variation between heights of peaks of absorption peaks in the absorption spectrum and a difference between locations of the peaks.

2. The film evaluation method of claim 1, wherein:
in the step (a), the electromagnetic waves are infrared radiation, and
in the step (b), the specific value is calculated from the shape of an absorption spectrum for the infrared radiation.

3. The film evaluation method of claim 2, wherein:
a plurality of reference infrared-absorption spectra are prepared in advance in accordance with film quality level, and
in the step (b), the reference infrared-absorption spectra and the infrared absorption spectrum of the film are compared with each other, thereby calculating the specific value.

4. The film evaluation method of claim 3, wherein in the step (b), multivariate analysis is performed based on the shapes of the reference infrared-absorption spectra and of the infrared absorption spectrum, thereby calculating the specific value.

5. The film evaluation method of claim 2, further comprising, prior to step (a), the step of irradiating the substrate with infrared irradiation, thereby measuring a reference infrared absorption spectrum, wherein:
in the step (a), the reference an infrared absorption spectrum is subtracted from the infrared absorption spectrum of the film and the substrate, thereby obtaining an infrared absorption spectrum of the film alone.

6. A temperature measuring method comprising the steps of:
(a) irradiating with electromagnetic waves a substrate on which a film is formed, thereby measuring an absorption spectrum for the electromagnetic waves, and
(b) calculating from the shape of the absorption spectrum a temperature at which the film has been grown,
wherein in the step (b), the temperature at which the film has been grown is calculated from a variation between heights of peaks of absorption peaks in the absorption spectrum and a difference between locations of the peaks.

7. The temperature measuring method of claim 6, wherein:
in the step (a), the electromagnetic waves are infrared radiation, and
in the step (b), the temperature at which the film has been grown is calculated from the shape of an absorption spectrum for the infrared radiation.

8. The temperature measuring method of claim 7, wherein:
a plurality of reference infrared-absorption spectra are prepared in advance in accordance with film-growing temperature, and
in the step (b), the reference infrared-absorption spectra and the infrared absorption spectrum of the film are compared with each other, thereby calculating the temperature at which the film has been grown.

9. The temperature measuring method of claim 8, wherein in the step (b), multivariate analysis is performed based on the shapes of the reference infrared-absorption spectra and of the infrared absorption spectrum, thereby calculating the temperature at which the film has been grown.

10. The temperature measuring method of claim 7, further comprising, prior to step (a), the step of irradiating the substrate with infrared irradiation, thereby measuring a reference infrared absorption spectrum,
wherein in the step (a), the reference infrared absorption spectrum of the substrate is subtracted from the infrared absorption spectrum of the film and the substrate, thereby obtaining an infrared absorption spectrum of the film alone.

11. The temperature measuring method of claim 6 wherein:
in the step (a), the substrate is placed in a film-growing apparatus in advance, and the film is formed on the substrate, and
in the step (b), the temperature at which the film has been grown is calculated as a temperature inside the film-growing apparatus.

12. A method for fabricating a semiconductor device including a film as an element forming the device, the method comprising the steps of:
(a) forming the film on a wafer placed in a film-growing apparatus,
(b) irradiating with infrared radiation the wafer on which the film has been formed, thereby measuring an infrared absorption spectrum,
(c) calculating from the shape of the infrared absorption spectrum a specific value corresponding to the quality of the film, and
(d) controlling conditions determined for the film-growing apparatus, in accordance with the specific value calculated in the step (c),
wherein in the step (b), the specific value is calculated from a variation between heights of peaks of absorption peaks in the absorption spectrum and a difference between locations of the peaks.

13. The semiconductor fabrication method of claim 12, wherein:
a plurality of reference infrared-absorption spectra are prepared in advance in accordance with film quality level, and
in the step (c), the reference infrared-absorption spectra and the infrared absorption spectrum of the film measured in the step (b) are compared with each other, thereby calculating the specific value.

14. The semiconductor fabrication method of claim 13, characterized in that in the step (c), multivariate analysis is performed based on the shapes of the reference infrared-absorption spectra and of the infrared absorption spectrum, thereby calculating the specific value.

15. The semiconductor fabrication method of any one of claims 12 through 14, wherein the specific value is a temperature at which the film has been grown.

16. A method for fabricating a semiconductor device including a film as an element forming the device, the method comprising the steps of:
(a) forming the film on a wafer placed in a film-growing apparatus;
(b) irradiating with infrared radiation the wafer on which the film has been formed, thereby measuring an infrared absorption spectrum;
(c) calculating from the shape of the infrared absorption spectrum a temperature at which the film has been grown; and
(d) controlling conditions determined for the film-growing apparatus, in accordance with the film-growing temperature calculated in the step (c),
wherein:
the film is a fluorine-doped silicon oxide film, and
in the step (c), the film-growing temperature is calculated from a difference in distance between an absorption peak of silicon oxide and an absorption peak of silicon fluoride in the infrared absorption spectrum.

17. The semiconductor fabrication method of claim 16, further comprising, prior to step (c), the step of preparing a plurality of reference infrared-absorption spectra in accordance with the film-growing temperature,
wherein:
in the step (c), the reference infrared-absorption spectra and the infrared absorption spectrum of the film measured in the step (b) are compared with each other, thereby calculating the film-growing temperature.

18. A method for fabricating a semiconductor device including a film as an element forming the device, the method comprising the steps of:
(a) forming the film on a wafer placed in a film-growing apparatus;
(b) irradiating with infrared radiation the wafer on which the film has been formed, thereby measuring an infrared absorption spectrum;
(c) calculating from the shape of the infrared absorption spectrum a temperature at which the film has been grown; and
(d) controlling conditions determined for the film-growing apparatus, in accordance with the film-growing temperature,
wherein:
the film is a fluorine-doped silicon oxide film,
the method further comprises, prior to step (c), the step of preparing a plurality of reference infrared-absorption spectra in accordance with the film-growing temperature,
in the step (c), pattern deviations are compared to each other, the pattern deviations resulting from a difference in a maximum absorption value at a peak, and in wavelength indicating the maximum absorption value, between each reference infrared-absorption spectrum pattern and the infrared-absorption spectrum pattern measured in step (b), and difference in distance between an absorption peak of silicon oxide and an absorption peak of silicon fluoride, thereby calculating the film-growing temperature.

19. The semiconductor fabrication method of claim 18, wherein in the step (c), multivariate analysis is performed based on the pattern deviations, thereby calculating the film-growing temperature.

* * * * *